United States Patent [19]
Benderev

[11] Patent Number: 6,110,099
[45] Date of Patent: *Aug. 29, 2000

[54] DEVICES AND METHODS FOR ASSESSMENT AND TREATMENT OF URINARY AND FECAL INCONTINENCE

[76] Inventor: Theodore V. Benderev, 26975 Magnolia Ct., Laguna Hills, Calif. 92653

[*] Notice: This patent is subject to a terminal disclaimer.

[21] Appl. No.: 09/116,696

[22] Filed: Jul. 16, 1998

Related U.S. Application Data

[63] Continuation-in-part of application No. 09/078,939, May 14, 1998, abandoned, which is a continuation-in-part of application No. 08/558,642, Nov. 13, 1995, Pat. No. 5,782,745.

[51] Int. Cl.[7] ........................................................ A61F 2/00
[52] U.S. Cl. ...................................... 600/30; 128/DIG. 25
[58] Field of Search ................ 600/29–32; 128/DIG. 25, 128/897–98, 774, 778, 775; 33/511, 512

[56] References Cited

U.S. PATENT DOCUMENTS

| | | | |
|---|---|---|---|
| 4,198,979 | 4/1980 | Cooney et al. | 128/295 |
| 4,246,901 | 1/1981 | Michaud | 128/295 |
| 4,681,572 | 7/1987 | Tokarz et al. | 604/329 |
| 4,889,533 | 12/1989 | Beecher | 604/330 |
| 5,188,120 | 2/1993 | White et al. | 128/778 |
| 5,437,649 | 8/1995 | Letchworth | 604/278 |
| 5,483,976 | 1/1996 | McLaughlin et al. | 128/885 |
| 5,513,660 | 5/1996 | Simon et al. | 128/885 |
| 5,603,685 | 2/1997 | Tutrone, Jr. | 600/29 |
| 5,611,768 | 3/1997 | Tutrone, Jr. | 600/29 |
| 5,697,886 | 12/1997 | Von Iderstein | 600/29 |
| 5,782,745 | 7/1998 | Benderev | 600/30 |

*Primary Examiner*—John P. Lacyk
*Attorney, Agent, or Firm*—Stetina Brunda Garred & Brucker

[57] ABSTRACT

Apparatus and methods for treating urinary and fecal incontinence, urinary drainage, and prolapse. In the first preferred embodiment, the invention comprises a device body insertable into an anatomical passageway and includes a stimulus-producing device disposed therein to provide a signal to the user to perform pelvic strengthening exercises or alternatively, an exercise monitoring device for monitoring exercise activity. In an embodiment for facilitating urinary drainage, there is provided an annular base panel coupled to an anchor member, the latter being designed to anchor the device within an anatomical passageway, such as the vagina. A port formed on the annular panel is provided to mate with the urethral meatus so that a continuous conduit is formed between the urethral meatus and the port. The various embodiments disclosed may further be utilized as pessary devices to provide structural support to the pelvis or utilized to construct customized pessary devices.

30 Claims, 5 Drawing Sheets

DEVICES AND METHODS FOR ASSESSMENT AND TREATMENT OF URINARY AND FECAL INCONTINENCE

RELATED APPLICATIONS

The present application is a continuation-in-part of pending U.S. patent application Ser. No. 09/078,939 entitled DEVICES AND METHODS FOR ASSESSMENT AND TREATMENT OF URINARY AND FECAL INCONTINENCE, filed May 14, 1998, now abandoned; which is a continuation-in-part of pending U.S. patent application Ser. No. 08/558,642 entitled DEVICES AND METHODS FOR ASSESSMENT AND TREATMENT OF URINARY AND FECAL INCONTINENCE, filed Nov. 13, 1995, now U.S. Pat No. 5,782,745 and further relies on the disclosure provided for in Disclosure Document No.'s 428, 948, having a date of receipt of Jan. 12, 1998, 431,157, having a date of receipt of Feb. 12, 1998, and 432,027, having a date of receipt of Jan. 30, 1998.

FIELD OF THE INVENTION

The present invention relates generally to medical devices and methods, and more particularly to devices and methods for evaluating and treating urinary and fecal incontinence by using proprioceptive neuromuscular facilitation and sensation, as well as devices and methods to facilitate urinary drainage and pelvic organ support.

BACKGROUND OF THE INVENTION

Urinary incontinence is believed to affect 15% to 30% of noninstitutionalized persons over the age of 60, and more then 50% of elderly persons (over the age of 60) who reside in nursing homes.

The presently available modes of treatment for urinary incontinence fall into four general categories, namely: i) management apparatus, ii) behavioral, iii) pharmacologic, and iv) surgical.

i. Management Apparatus for Incontinence

The management apparatus modes of treatment generally comprise absorbent and/or catheter structures worn by a user to retain any urinary and/or fecal incontinence. In their simplest forms, such devices comprise diaper-like structures which must be periodically changed by the user. Although such management apparatus has proven generally effective in masking the results of incontinence, they are uncomfortable to wear, difficult to change, and oftentimes fail during use thereby embarrassing the user.

ii. Behavioral Treatment for Incontinence

The use of behavioral training as a treatment for urinary and/or fecal incontinence can involve numerous behavioral techniques including; bladder re-training (e.g., voiding on a timed schedule), and/or the performance of exercises (e.g., Kegel exercises) to strengthen and retrain a group of muscles collectively known as the "pelvic floor muscles." As an adjunct to these behavioral training techniques, various intravaginal and/or intra-anal devices may be utilized to facilitate the performance of such pelvic muscle training exercises. Such intravaginal and/or intra-anal devices have included simple weighted apparatus such as pessaries or intravaginal cones. Exemplary of such prior art pessaries are the pessaries manufactured by Milex Wester Company, 639 North Fairfax, Los Angeles, Calif. 90036; while an example of such weighted cone device is the "FEMINA" cone manufactured by Dacomed Corporation, 1701 East 79th Street, Minneapolis, Minn., 55425. Other types of prior art devices include pneumatic-type devices and electromyographic (EMG) transducers or sensors which are insertable into or placed just outside of the vagina and/or anus to obtain EMG data indicative of baseline pelvic floor muscle tone and/or contraction(s) of the pelvic floor muscles during the performance of specific muscle contraction exercises. Such EMG data may be usable for diagnostic purposes as well as for monitoring the performance and/or effect of muscle training exercises. Some EMG devices have included means for providing visual or auditory feedback to assist the patient in the performance of pelvic floor muscle exercises (e.g., Myoexorciser III, available from Verimed 1401 East Broward Boulevard, Suite 200, Fort Lauderdale, Fla. 33301 and the PRS 8900 Office System made by Incare Medical Products, Libertyville, Ill. 60048.

Additionally, the prior art has included at least one transvaginal electrical stimulation device which is operative to deliver periodic or timed electrical stimulation to the pelvic floor muscles and nerves. Such electrical stimulation causes involuntary contraction of the pelvic floor muscles and may serve as an adjunct to the performance of volitional exercise and/or other behavioral training techniques (e.g., Microgyn II Stimulation Device, InCare Medical Products, Division of Hollister Incorporated, 2000 Hollister Drive, LibertyVille, Ill., 60048 and also the Innova Feminine Incontinence Treatment System available from EMPI, Inc., 1275 Grey Fox Road, St. Paul, Minn. 55112).

Although some of or all of the above-described devices and systems for exercise and/or training of the pelvic floor muscles may be effective in the treatment of urinary incontinence, there remains a need for the development of improved devices and systems which are capable of strengthening and training the pelvic floor muscles in minimal time, with minimal assistance from physicians or other health care professionals as well as a system which serves to remind a user to perform muscle exercises and to provide proprioceptive input to assist the user in exercising and strengthening desired muscles.

iii. Pharmacologic Treatment for Incontinence

The prior art pharmacologic treatment of urinary incontinence typically involves the long term administration of drugs. Such pharmacologic treatment may result in drug-related side effects. Also, the efficacy of such pharmacologic treatment is frequently limited and largely dependant upon the patient's ability or willingness to comply with the prescribed drug dosage schedule.

iv. Surgical Treatment for Incontinence

The prior art surgical modes of treatment of urinary incontinence typically involve the performance of one or more major surgeries procedures under anesthesia. These major surgical procedures can be associated with significant risks and may sometime result in post-surgical failure, infections, or other complications. Also, these surgical procedures typically result in significant expense to the patient and/or the patient's third party insurer.

As such, there exists a substantial need in the art for an incontinence treatment system and methodology which reduces or eliminates the need for prior art management apparatus and/or surgical treatments, reduces the use of long-term drug administration, accentuates muscle strengthening and training while reminding a patient to conduct muscle strengthening exercise, as well as provide a proprioceptive input to assist the patient in contracting the appropriate muscles and/or muscle groups necessary for the effective treatment of incontinence.

Additionally, in connect therewith, there is a need in the art to facilitate the drainage of urine from the bladder of a patient. In this regard, systems to collect urine for quantitative and qualitative analysis and facilitate bladder drainage, which typically comprise an indwelling rubber catheter disposed within the urethra of the patient, such as a Foley catheter, suffer from the draw back of being difficult and uncomfortable to utilize and further, are less than optimal to collect urine, particularly with respect from female patients. Additionally, it is well recognized that long-term use of indwelling catheters is a significant source of bacteriuria and UTI (urinary tract infection). Indeed, there are reported cases of sepsis and death from severe UTI caused by such indwelling catheters.

A condition further related to incontinence is prolapse, i.e., the slipping down of an organ or part from its normal position, of the uterus, bladder (cystocele), vagina, and/or rectum (rectocele). With respect to prolapse of the uterus, such condition occurs when the uterus falls into the vagina due to stretching and laxity of its supporting structures. Cystocele/rectocele are conditions where the bladder/rectum herniate into, and at times out of, the vagina.

Typically, pessary devices are utilized to provide the necessary pelvic support for the various aforementioned conditions. Such pessary devices, which are well-known to those skilled in the art, can take the form of ring pessaries, folding pessaries, such as the Hodge folding pessary or Risser folding pessary, cube pessaries, and gellhorn pessaries, all of which are designed to be inserted within the anatomical passageway that is the subject of the prolapse and remain resident therein to provide the necessary structural support.

While such pessary devices are generally effective in providing the necessary structural support to thus maintain the organ or part of the body affected by the prolapse in its normal position, such pessary devices currently in use suffer from numerous drawbacks. Specifically, such devices are ill-suited to remain firmly anchored within the anatomical passageway within which the same are received. Moreover, such conventional pessary devices are difficult to be inserted and withdrawn from their intended anatomical passageway. Still further, most conventional pessary devices poorly adapt to the specific contours of the specific anatomy of the given patient and are thus unable to form a "custom" fit, which would be most ideal for providing the optimal degree of structural support. Accordingly, there is further a need in the art for a pessary device that can be easily inserted within an anatomical passageway and remain firmly anchored therein. There is also a need for a pessary device capable of forming a custom-fit to a given patient's particular specific anatomy such that optimal support structure can be formed.

SUMMARY OF THE INVENTION

In accordance with the present invention, there is provided a device which is insertable into a pelvic anatomical passageway of a patient (e.g., the vagina or anus) to identify target pelvic floor muscles and/or muscle groups responsible for fecal and/or urinary incontinence and facilitate the performance of exercises to strengthen the same. According to a first preferred embodiment, the device generally comprises a device body having a generally arrowhead-shaped distal portion having a flattened, generally cross-sectional configuration, and intermediate shaft portion, and a proximal base portion that is sized and contoured to be inserted into a pelvic anatomical passageway. The distal portion is specifically designed to anchor the device body within the target anatomical passageway with the intermediate and proximal portions of the device body being designed to extend therefrom to thus facilitate manual manipulation of the device body during insertion and withdrawal of the device from the anatomical passageway.

The distal portion is alternately transitionable between a non-stimulus mode wherein the distal portion simply remains at rest while anchored within an anatomical passageway, and a stimulus mode configuration whereby a perceptible stimulus is produced against the region of the anatomical passageway to which the distal portion of the device is anchored to thus remind the patient to perform the pelvic wall muscle exercises. The stimulus produced in the stimulus mode is preferably generated from a stimulus producing device disposed within the distal portion of the device body, and may preferably comprise a vibrator or pressure-exerting device.

With respect to the pressure-exerting device, such device is specifically designed to alternately transition between i) a rest mode configuration wherein such device causes the distal portion of the device body to exert no more than a base line amount of pressure against a predetermined region of the anatomical passageway within which the device body is located and, ii) an exercise mode configuration wherein the device causes the distal portion of the device body to exert more than the base line amount of pressure against the predetermined region of the anatomical passageway within which the device body is inserted.

A small battery and battery-powered motor may be mounted on or within the device to drive the transformation of the device between the stimulus mode configuration and the non-stimulus mode configuration. Additionally, a timer or other type of switching apparatus may be mounted on or within the distal portion of the device to trigger and control the timing, duration, repetitions, and frequency of transformation of the device between the rest mode configuration and the exercise mode configuration, at predetermined times. Still further in accordance with the invention, a remote controlled triggering device may be used in addition to, or in place of, a timer or other control apparatus mounted on or within the device. Such remote control apparatus may be utilized to trigger, control and/or schedule all operational parameters of transformation of the device, back and forth, between its rest mode configuration and exercise mode configuration, from a remote location.

In an alternative configuration, the distal portion, as opposed to being alternately transitionable between stimulus and non-stimulus modes, has disposed therewithin an exercising monitoring device designed and configured to monitor the frequency and duration the patient performs the prescribed strengthening exercises. Such monitoring device further identifies which muscle or muscle groups are actually being exercised, as well as evaluates the progress made by the patient in strengthening the same. According to one particular embodiment, such exercise monitoring device may utilize biofeedback to provide the patient with a perceptible signal consistent with the frequency and effectiveness of the patient's performance of the exercise regimen to thus enable the patient to keep track of and consciously control the progress made in practicing such exercise regimen.

In a second preferred embodiment, the device comprises the combination of a device body constructed in accordance to the first embodiment, but further includes a remote enclosure coupled thereto via a cord. Within the enclosure is a power source, timing circuit electronics, and switching devices to enable the user or healthcare practitioner to selectively implement the operation of a stimulus producing apparatus, and more particularly, a bilateral pressure-exerting mechanism, dispose within the distal portion of the device body, to thus generate a perceptible stimulus to thus remind the user to perform the desired strengthening exercises.

In a third preferred embodiment, the device comprises a device body having the distal, intermediate and proximal portions, as per the first and second embodiments, and further includes a novel stimulus producing apparatus comprising at least one, and preferably a plurality of protuberances mounted on respective ones of a pair of gears disposed within the distal portion of the device body. A third gear mounted to an axle and disposed intermediate the first and second gears is provided to selectively rotate the gears having to protuberances formed thereon such that the protuberances bulge through and rotate about the distal portion of the device body. As a result, there is thus generated a perceptible stimulus to thus remind the user to perform the desired strengthening exercises.

In yet another preferred embodiment, the device comprises a device body having the distal, intermediate, and proximal portions discussed above, in combination with a novel pressure-exerting stimulus producing apparatus. With respect to the latter, such stimulus producing apparatus comprises the combination of a pair of pressure-exerting arm members or flippers disposed within the distal portion of the device body that are operative to extend outwardly therefrom, such that such pressure is exerted upon the surrounding anatomy to which the distal portion is anchored. The increased pressure exerted thereby thus generates the perceptible stimulus necessary to remind the user to perform the necessary strengthening exercises for the target muscles and/or muscle groups.

There is additionally provided in an alternative embodiment a device capable of being anchored within an anatomical passageway for facilitating urinary drainage. According to such embodiment, the device comprises of the combination of a generally annular base having a flexible mushroom-shaped anchor member affixed thereto, the latter being designed and configured to nest and become seated within an anatomical passageway. A port formed upon the annular base is designed and configured to be axially aligned with and sealed to the urethral meatus once the anchor member is seated within the passageway so that the flow of urine from the bladder of the user is facilitated.

In a further preferred embodiment, there is provided a device for facilitating urinary drainage that likewise incorporates a generally annular base having an anchor member formed thereon, the latter being selectively transitional between a first insertion mode, wherein the device assumes a first insertion configuration which enables the device to be easily inserted within the anatomical passageway, and an anchor configuration, wherein such anchor member selectively expands and compresses radially about the anatomical passageway to thus cause the same to become firmly anchored thereat. As in the above embodiment, a port formed on the annular base is designed and configured to be axially aligned with and sealed to the urethral meatus once the anchor member is seated within the passageway.

In addition to facilitating urinary drainage, such anchor mechanism may be utilized independently to serve as a pessary device to treat prolapse of either the uterus, rectum, or vagina. Such anchoring device is particularly well-suited to cause the urethra to assume its proper physiological position. The anchoring device may be further utilized to develop a custom pessary that is specifically designed and configured to accommodate and adapt to the anatomy of a particular individual.

Still further in accordance with the invention, there are provided methods of treating urinary and/or fecal incontinence in a patient. In general, the method comprises the steps of inserting a device of the forgoing character into either the vagina or anus, and utilizing the device to intermittently deliver increased stretch/resistance/vibration/pressure or heat stimuli against the wall and/or adjacent muscles of the vagina or anus to facilitate the performance of pelvic muscle strengthening exercises by the patient in whom the device is inserted. Additionally in accordance with the present invention, there is provided a method for facilitating drainage of urine from the bladder of an individual, and particularly female. Such method comprises the steps of inserting an anchoring device of the foregoing character into an anatomical passageway and aligning and mating a port with the urethral meatus of the patient to thus provide a continual passageway through which urine may pass from the body. Still further, there is provided novel pessary devices and methods for treating prolapse of either the uterus, rectum, or vagina, as well as devices and methods measuring and determining the specific dimensions of an anatomical passageway to form custom pessary devices for use therewith.

BRIEF DESCRIPTION OF THE DRAWINGS

These, as well as other features of the present invention, will become more apparent upon reference to the drawings, wherein.

DETAILED DESCRIPTION OF THE PREFERRED EMBODIMENTS

The following detailed description and the accompanying drawings are provided for the purpose of describing certain presently preferred embodiments of the invention only, and are not intended to limit the scope of the claimed invention in any way.

Figure 1:
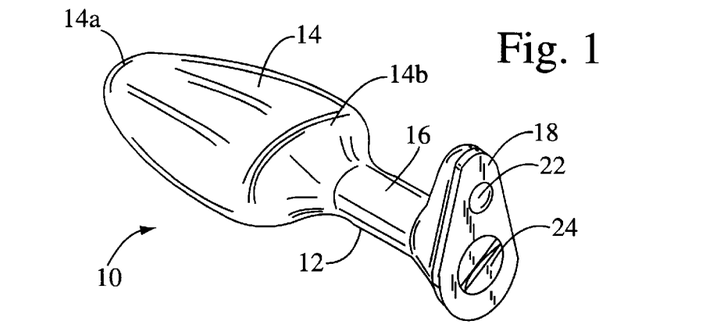
FIG. 1 is a perspective view of a first embodiment of a urinary and/or fecal incontinence treatment device of the present invention.
Figure 2:
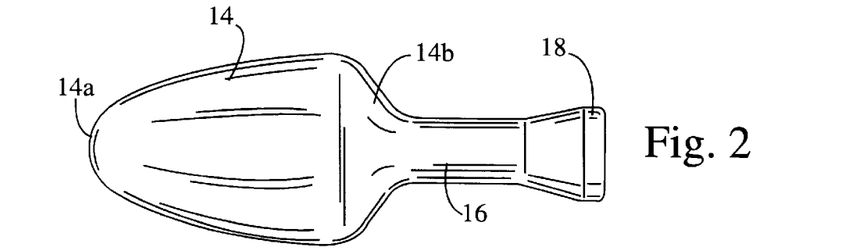
FIGS. 2 is a top view of the incontinence treatment device depicted in FIG. 1.

Referring now to the drawings, and initially to FIG. 1 there is shown a first embodiment of a intra-vaginal or intra-anal device 10 of the present invention which may be utilized for the effective treatment of both urinary and fecal incontinence in female as well as male users or patients. The device 10 is operative to identify target pelvic floor muscles and muscle groups responsible for urinary and/or fecal incontinence and provide timed or periodic changes in stimuli, such as pressure or vibration thereto. The stimulus created by the device 10 will promote proprioceptive neuromuscular facilitation and serve as a reminder to perform, and/or will facilitate the performance of, muscle-strengthening exercises of the target muscles (e.g., Kegel exercises) by the patient in whom the device 10 is indwelling. A more detailed description of proprioceptive neuromuscular facilitation is found in Sullivan, P. E., et al.: "An Integrated Approach To Therapeutic Exercise", published by Reston Publishing Co., Reston, Va., pages 161–183, the disclosure of which is expressly incorporated herein by reference.

As illustrated, the first embodiment of the device 10 comprises an elongate device body 12 having a generally conical or arrowhead-shaped distal portion 14, an intermediate shaft portion 16, and a proximal based portion 18. The distal-most end 14a of distal portion 14 enables the device body 12 to easily penetrate and become inserted within the intended pelvic anatomical passageway (e.g., vagina, anus). As the distal portion 14 of the device body is advanced into the anatomical passageway, the base portion thereof 14b provides for frictional retention radially about the contours of the anatomical passageway such that the device may be captured and anchored against the muscles and tissue surrounding the body opening. As will be recognized, intermediate shaft portion 16 and proximal base portion 18 provide means to enable the user or healthcare practitioner to accurately position the device body 12 within the target anatomical passageway, as well as remove the same therefrom.

Figure 5:
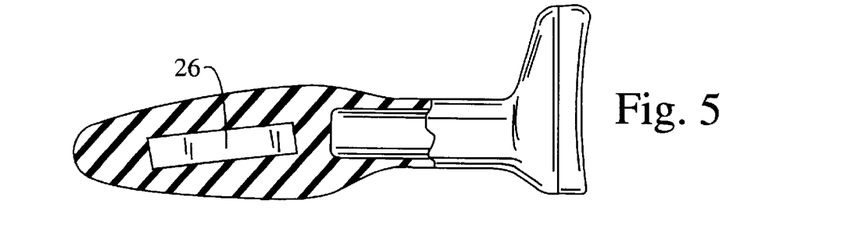
FIG. 5 is a side view of the incontinence treatment device depicted in FIG. 3, partially in cross-section.

In order to provide the necessary stimulus to the patient to thus facilitate the performance of pelvic muscle exercises, there is formed within the distal portion 14 of the device body a stimulus-producing device 26, as depicted in FIG. 5. Such stimulus-inducing device 26 may take the form of those devices disclosed in co-pending patent application Ser. No. 08/558,642, the teachings of which are expressly incorporated herein by reference.

Specifically, such stimulus producing device 26 may take the form of a vibrator or, alternatively, a pressure-exerting device which causes the distal portion 14 to selectively expand to a sufficient degree so as to produce a perceptible physical stimulation to the patient. As discussed in the parent application, such pressure stimulation device 26 is preferably transitionable between i) a rest mode configuration wherein the device causes the distal portion 14 of the device body 12 to exert no more than a baseline of pressure against the region of the anatomical passageway within which the distal portion 14 of the device body 12 is located and ii) an exercise mode configuration wherein the pressure producing device causes the distal portion 14 of the device body 12 to exert more than the baseline amount of pressure against the predetermined region of the anatomical passageway within which the distal portion 14 of the device body 12 is inserted.

The patient will sense the vibration and/or exertion of pressure stretch or resistance against the vaginal or anal wall and/or adjacent muscles to thus identify these muscles sought to be strengthened. The patient will be thereby reminded and compelled to volitionally perform the prescribed pelvic wall muscle exercises. With respect to the incorporation of either a pressure-exerting or vibrational mechanism, the pressure, stretch and/or resistance thereby created will thus improve the muscle-strengthening efficacy of such exercises by proprioceptive neuromuscular facilitation.

After a predetermined time (e.g., sufficient time for the patient to perform the prescribed muscle exercise) has expired, or upon delivery of other triggering input (e.g., a remote control signal), the stimulus provided by the stimulus-producing device 26 is selectively terminated, i.e., the stimulus-producing device 26 is caused to assume a rest or non-operational mode.

After the stimulus producing device 26 has returned to such "non-operative" mode, the device 10 may remain in such mode and indwelling within the vagina or anus. Upon expiration of a predetermined time period or upon receipt of a triggering input signal, such as may be received from a switch 22 formed on the device or designated event the stimulus producing device 26 will become actuated to thus assume its "operative" mode, whereby the device 10 will return to its exercise mode for an additional period of time.

Figure 3:
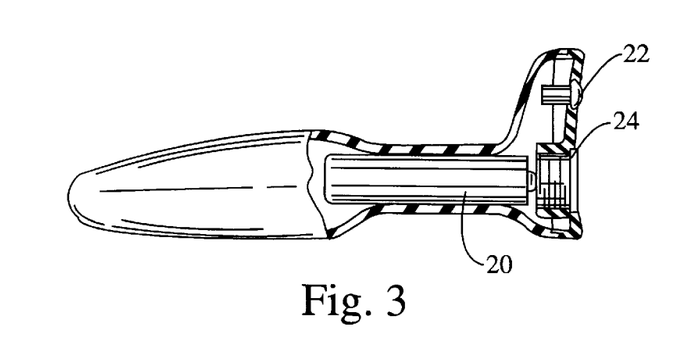
FIG. 3 is a side view of the incontinence treatment device depicted in FIG. 1, partially in cross-section.
Figure 4:
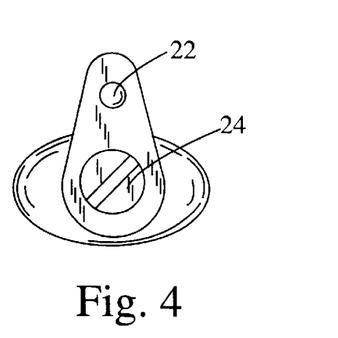
FIG. 4 is a rear view of the incontinence treatment device depicted in FIG. 1.

The above-described sequence of events may be repeated on any prescribed schedule, or at any prescribed frequency or variable extension, so long as the device 10, and more particularly the distal portion 14 thereat, remains anchored within the vagina or anus. As will be recognized, a power source, such as a battery 20 shown in FIG. 3, will be provided to thus enable the stimulus producing device 26 to selectively transition between its operative and non-operative modes. As discussed above, a small triggering and control apparatus, such as a switch 22 or timer (not shown), may also be formed upon or disposed within the device body and connected to the stimulus producing device 26 to cause the same to actuate or assume its operative mode on a predetermined time schedule. Alternatively, a remote control or telemetric switch 22 or signal receiver may be utilized to receive remote control signals and to schedule the operation of the device by actuating or de-actuate the stimulus producing device 26, as desired.

In an alternative configuration, the device 26 disclosed within the distal portion 14 may take the form of an exercise monitor that is specifically designed to keep track of the frequency the patient performs the prescribed muscle strengthening exercises and the duration such exercises are performed. Such monitor may further identify which muscle or muscle groups the patient is, in fact, exercising and quantify the increased strengthening of those muscles over time. In this regard, the exercise monitoring device, which may take the form of the embodiment depicted in FIGS. 8–10, discussed more fully below, may be provided with pressure sensing devices attached thereabout such that when the patient performs the appropriate exercises, the pressure exerted upon the distal end 14 of the device by the muscle groups surrounding the anatomical passageway, including how that pressure is distributed about a distal end 14, will thus enable the monitoring device 26 to provide such information.

The data obtained from such exercise monitoring device 26 may be utilized to produce a quantifiable signal to the patient to thus enable the patient to consciously control, via biofeedback, the progress and effectiveness sought to be obtained by practicing a prescribed exercise regimen. Such data may be further utilized by healthcare professionals to monitor the patient's progress, as well as help the healthcare professional to give provide coaching or medical advice to thus optimize the results of practicing such exercise regimen.

Because of its contoured design, the device body 12 is ideally adapted to remain anchored within the anatomical passageway for extended periods of time and not interfere with the ability of the user to engage in normal activities, such as sitting, or walking. However, as may become necessary, the device body 12 may be removed from the anatomical passageway within which it is placed by manually grasping the base portion 18 (and intermediate shaft portion 16) and pulling rearwardly to thus dislodge the distal portion 14 of the device body 12 from its anchored position within the anatomical passageway. Additionally, to the extent that it becomes necessary to access the interior of the device body 12, and more particularly the battery 20 and/or stimulus-producing device/exercise monitor 26 disposed therewithin, there may preferably be provided a port 24 formed upon the proximal base portion 18 of the device body 12.

Figures 6, 7:
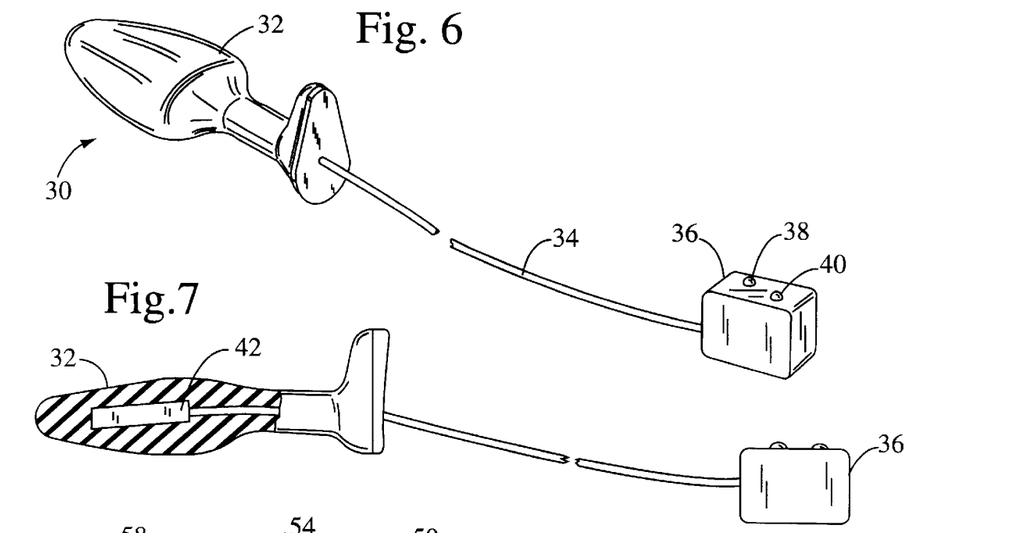
FIG. 6 is a perspective view of a urinary and/or fecal incontinence treatment device constructed in accordance with a second preferred embodiment of the present invention.
FIG. 7 is a side-view of the incontinence treatment device depicted in FIG. 5, the device body thereof shown by partial cross-section.

Referring now to FIGS. 6–10, a second alternative embodiment of the device 30 is shown. As per the first embodiment, the second embodiment 30 incorporates a device body 32 that is preferably formed to have the distal, intermediate, and proximal sections discussed above. In such embodiment, however, there is further provided a remote inclosure 36 that is coupled to the device body 32 via cord 34, which may be electrical. The remote enclosure 36 is utilized to house a power source, i.e., batteries, timing circuit electronics, and dedicated switches, namely, a power button 38 and stimulus control button 40 to thus provide external switching means to enable the patient or healthcare provider to selectively implement activation of a stimulus-producing device 42 disposed within the device body 32, and preferably within the distal portion thereof, as shown in FIG. 7.

As per the first embodiment, the stimulus producing device 42 disposed within the device body 32, and more particularly the distal portion thereof, will be caused to alternate between providing a stimulus, to thus remind the patient to perform the prescribed pelvic wall muscle exercises, and a non-operational mode where such stimulus is not produced. In this regard, such stimulus-producing device 42 may preferably take the form of a pressure-exerting mechanism, such as those disclosed below and in the pending parent application. Moreover, such device 42 may alternatively comprise an exercise monitoring device to quantify and evaluate the patient's progress in performing such exercises, and may further provide biofeedback to enable the patient to consciously control and optimize the performance at such exercises.

Advantageously, however, because of the external nature of the remote enclosure 36, the device 42 disposed within the device body 32 may be easily and readily activated without the need to come into close contact with the anatomical passageway within which the device body 32 is received, which can thus preserve the patient's dignity and minimize embarrassment for both the patient and healthcare provider.

It is further contemplated that such remote enclosure 36, because of the incorporation of the timing electronics, may further be utilized to enable the device 30 to operate in an automatic mode, whereby an operational signal within the remote enclosure 36 is generated at predetermined times which thus causes the stimulus producing device 62 to produce an exercise-inducing stimulus pursuant to the terms of a set regimen. As will be recognized, this second embodiment of the present invention, and more particularly the remote enclosure 36 thereof, will further preferably include a timer or controller which functions to selectively cause the device 30 to go from a rest configuration to an operative configuration as desired.

Figures 8, 9, 10:
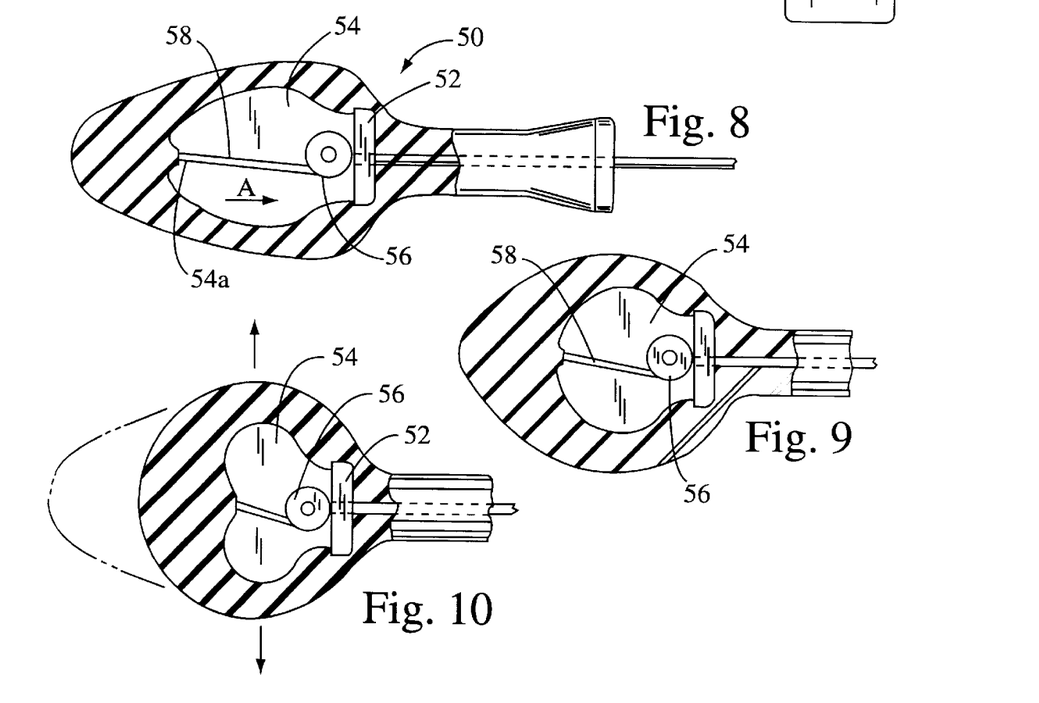
FIG. 8 is a top view, partially in cross-section, of the device body portion of the incontinence treatment device depicted in FIG. 5.
FIG. 9 is a top sectional view of the device body of FIG. 8 assuming an intermediate pressure stimulus mode.
FIG. 10 is the distal portion of the device body depicted in FIG. 9 assuming a fully-operative pressure stimulus configuration.

As illustrated in FIGS. 8–10, there is shown an embodiment of a pressure-exerting system 50 formed within the distal portion of the device body 32 for producing the stimulus to facilitate the performance of pelvic muscle strengthening exercises. According to such system 50, there is provided an elongate base 52 anchored within a generally annular cavity 54 formed within the distal portion of the device body. Preferably, such elongate base 52 is affixed within the distal portion of the device body just beyond the juncture between the distal portion and the intermediate shaft portion. A motor 56 having a cord 58 apparatus affixed thereto is anchored to the elongate base 52. The motor 56 is designed to rotate in a fashion such that cord 58 affixed thereto is consequently caused to be drawn in. The cord 58 is joined to the distal-most point 54a of the annular cavity 54 such that when the cord 58 is caused to rotate in a counter-clockwise fashion, the cord 58 thus causes the annular cavity to be drawn inwardly as indicated by the direction A.

By virtue of being drawn inwardly, the annular cavity 54 consequently exerts an outwardly biasing force to the sides of the distal portion of the device body 32, to thus cause the same to protrude outwardly in the manner shown which thus produces the desired stimulus.

As will be recognized, motor 56 will necessarily rotate in both clockwise and counter-clockwise directions so as to enable the device body to selectively transition between rest mode and exercise configurations. In this regard, and as shown in FIG. 8, the pressure-exerting system 50 is shown in a rest mode configuration such that the system 50 is exerting no more than a baseline amount of pressure to the periphery of the annular cavity 54 formed within the distal portion of the device body. When necessary to cause the device to exert outward pressure, stretch or resistance to the anatomical passageway, motor 56 is caused to rotate in the manner discussed above, to thus cause cord 58 to gradually impart the pressure stimulus as sequentially depicted in FIGS. 9 and 10. To return the device to its rest mode configuration, motor 56 will rotate in an opposite direction, thereby allowing the cord 58 to relax the annular cavity and thus enable the same to return to the rest mode configuration. Such transition can be selectively controlled via signals received from the external enclosure 36.

The embodiment depicted in FIGS. 7–10, as discussed above, may alternatively function as an exercise monitoring device for quantifying and evaluating the patient's progress in performing the prescribed pelvic muscle strengthening exercises. As opposed to exerting a pressure stimulus, such alternative configuration monitors exercise activity by selectively deforming during the performance of muscle strengthening exercises. Specifically, the patient, by virtue of performing such exercises, exerts pressure upon the distal end 32 of the device which causes the same to assume an altered shape. Such deformation thus alters the spacial dynamics of chamber 54, which can be measured via the change in length of cord 58, as schematically depicted in FIGS. 8–10. Accordingly, as the patient performs the necessary exercises, the duration of such exercises, as well as which muscles are, in fact, being exercised can be determined.

Figures 11, 12:
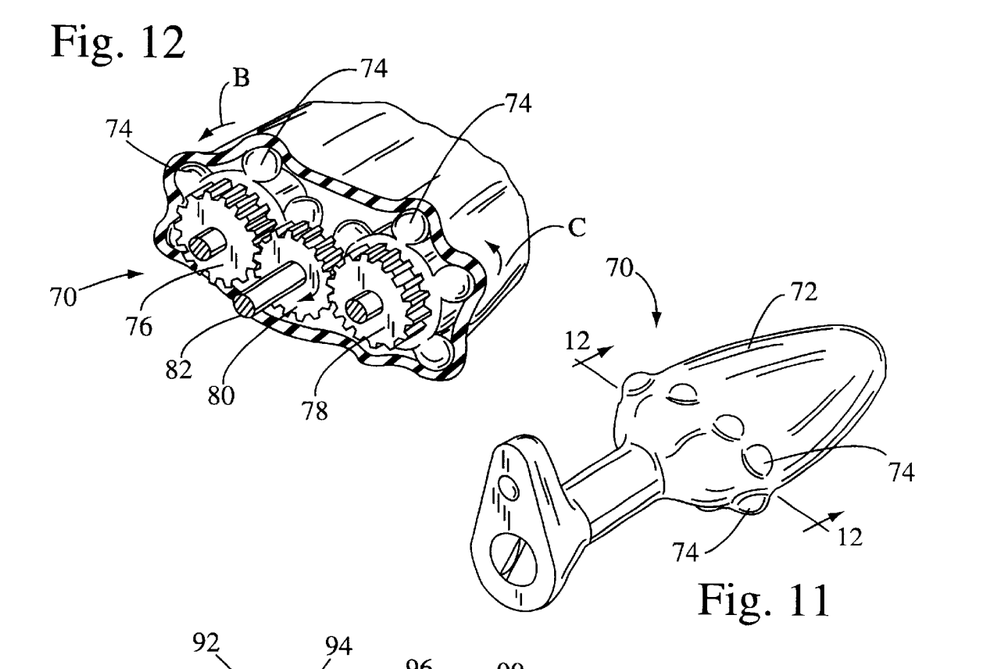
FIG. 11 is a perspective view of a urinary and/or fecal incontinence treatment device constructed in accordance with a third preferred embodiment of the present invention.
FIG. 12 is a view taken along the line 12—12 of FIG. 11.

In FIGS. 11 and 12, an alternative pressure-exerting system 70 constructed in accordance to a preferred embodiment of the present invention is depicted. As will be recognized, such system 70 will be mounted within the distal portion of the device body 72 to thus produce a pressure stimulus when desired at predetermined times. As illustrated, the system 70 comprises a plurality of protuberances 74 that radially bulge out of and rotate about the distal end of the device body 72. By virtue of the rotational movement to the protuberances 74, there is imparted thereby a pressure stimulus that identifies the target muscle or muscle groups sought to be strengthened and reminds the patient to perform the strengthening exercises therefor. As seen in FIG. 12, the plurality of protuberances 74 are mounted upon respective ones of a pair of gears 76, 78 mounted on opposed sides of one another within the distal portion of the device body 72. A third gear 80 mounted upon an axle 82 and disposed between the first and second gears 76, 78 drives the same to rotate in the directions B and C shown. As will be recognized, a motor (not shown) coupled to the axle 82 will be provided to drive the aforementioned gears.

By virtue of such rotational movement, the plurality of protuberances 74 mounted upon the first and second gears 76, 78 will impart a pressure stimulus to the distal portion of the device body 72, which will in turn cause the distal portion of the device body to impart the desired stimulus to the anatomical passageway within which the device body is anchored.

Figures 13, 14:
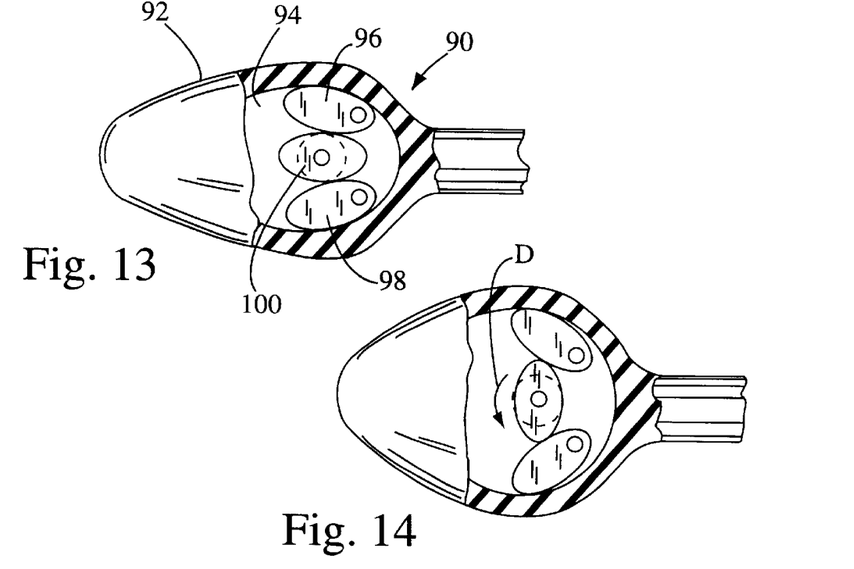
FIG. 13 is a top view, partially in cross-section, of the distal portion of the device body of the incontinence treatment device of the present invention further depicting therein a novel pressure-exerting apparatus constructed in accordance with a preferred embodiment, the latter assuming a rest mode configuration.
FIG. 14 is a top view, partially in cross-section, of the distal portion of the device body in FIG. 13 with the pressure-exerting apparatus assuming an operative configuration.

Referring now to FIGS. 13 and 14, and initially to FIG. 13, there is shown an alternative embodiment of a pressure stimulus system 90. As with the other aforementioned pressure-exerting systems, the system 90 depicted is selectively transitional between a rest mode configuration and an exercise configuration. The system 90 comprises a pair of arm members 96, 98 disposed within an annular cavity 94 formed within the distal portion of the device body 92. The arms 96, 98 are maintained in abutment with a pressure-exerting member 100 disposed therebetween. The pressure-exerting member 100, which preferably takes form of an oblong member as shown, may be caused to rotate such that in a first configuration, shown in FIG. 13, the arm members 96, 98 disposed on either side of the pressure-exerting member 100 are inwardly oriented within the annular cavity. When the pressure-exerting member is caused to rotate in the direction indicated by the letter D, as depicted in FIG. 14, the arms disposed on either side thereof are caused to expand outwardly, thus causing the distal portion of the device body 92 to extend outwardly and press against the target tissue and muscles and axially compress thereabout.

Figure 15:
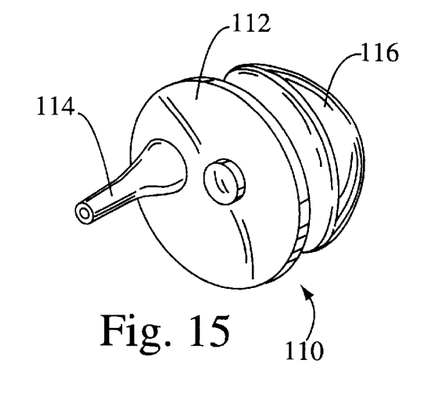
FIG. 15 is a perspective view of a urinary incontinence treatment device constructed in accordance with a fourth preferred embodiment of the present invention.
Figure 16:
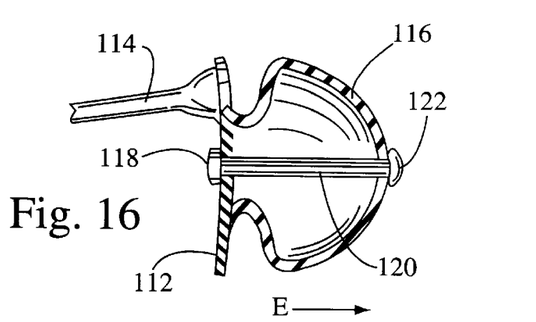
FIG. 16 is a side-view of the incontinence treatment device depicted in FIG. 13, shown partially and cross-section, with the device assuming a first pre-insertion configuration.

Referring now to FIGS. 15–19, and initially to FIG. 15, there is shown a fourth embodiment 110 of an incontinence treatment device specifically designed and adapted to facilitate the drainage of urine from the bladder and urethra of a patient. As illustrated, such embodiment 110 comprises an annular base panel 112 upon which is formed a port 114, which may have a generally frusto-conical shape and, as discussed in more detail below, is specifically designed and configured to axially align and seal about the urethral meatus of the user.

Attached behind the annular base panel 112 is a rubberized, mushroom-shaped anchor member 116. As more clearly shown in FIG. 16, the anchor member 116 is attached to the annular base panel 112 via an elongate coupling member 120 having opposed retention hubs 118, 122 formed thereon, the latter providing means to secure the anchor member 116 to the annular base panel 112.

Figure 17:
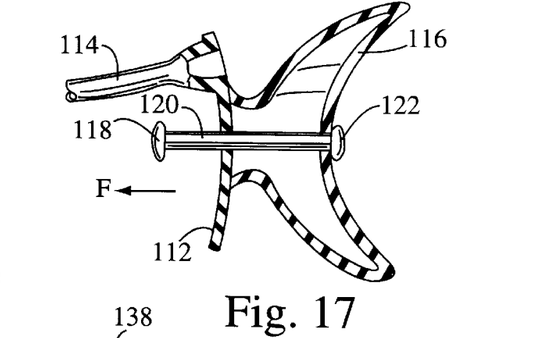
FIG. 17 is a side-view of the incontinence treatment device depicted in FIG. 14 shown in an anchored configuration.

Due to its flexible nature, the anchor member 116 is radially flexible thereabout and may be selectively deformed and inverted, as illustrated in FIG. 17, such that the anchor member 116 substantially expands radially outward to form a tight, annular fit within an anatomical passageway. In this regard, in FIG. 16, the device 110 is shown in an insertion mode whereby the mushroom-shaped anchor member 116 may be advanced into an anatomical passageway, as indicated by the letter E. Once advanced sufficiently into an anatomical passageway, the annular base panel 112 and/or retention hub 118 is pulled rearwardly as indicated by the letter F a sufficient distance to cause the anchor member 116 to deform and expand radially outward to thus invert upon itself in the manner shown. By virtue of the attachment of the annular base panel 112 to the anchor member 116 via coupling member 120, the annular base panel 112 is maintained in abutment about the periphery of the opening of the vagina.

Figure 18:
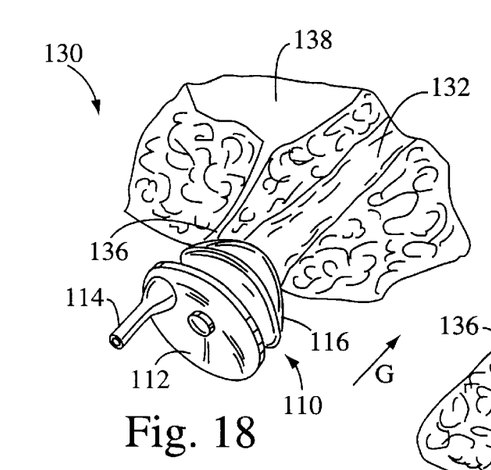
FIG. 18 is a cross-sectional view of a female pelvic region whereby the incontinence treatment device depicted in FIG. 13 is shown perspectively being inserted within the vaginal lumen thereof.
Figure 19:
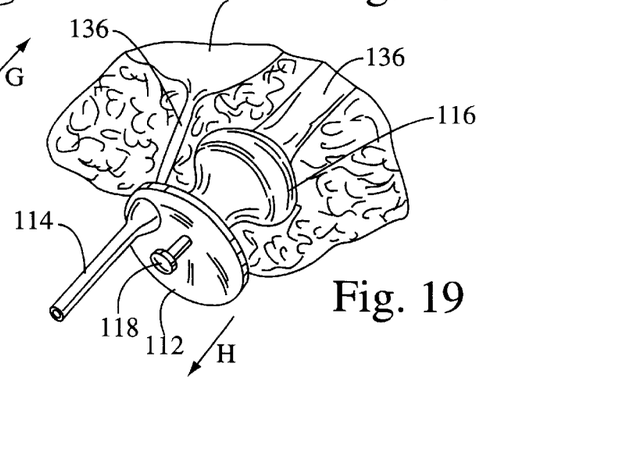
FIG. 19 is a perspective view of the incontinence treatment device of FIG. 16 shown anchored within the vaginal lumen of the pelvic region.

With reference to FIGS. 18 and 19, there is shown the device 110 according to the fourth embodiment as shown being deployed in relation to a female pelvic region 130. As illustrated, the device 110, and more particular the mushroom-shaped anchor member 116 thereof is advanced into the vaginal lumen 132 as indicated by the letter G. In this regard, the annular base panel 112 and frusto-conical port 114 formed thereon are specifically sized to enable the latter to become aligned and mate with the urethral meatus 136 once the mushroom-shaped member 116 is sufficiently advanced and anchored within the vaginal lumen 132.

Thereafter, the annular base panel 112 or retention hub 118 is pulled rearwardly as indicated by the letter H to thus cause the anchor member 116 to invert upon itself in the manner illustrated in FIG. 19. The inversion of the annular anchor member 116 within the vaginal lumen 132 causes the anchor member 116 to radially compress about the lumen 132, which thus serves to anchor the device in position.

The annular base panel 112 will selectively position the port 114 to be aligned with the urethral meatus 136. Once so aligned with the urethral meatus 136, the port may be radially sealed thereabout by any of a variety of methods well-known in the art. The patient may expel urine stored within the bladder 138 through the urethral meatus 136 and the port 114 to thus facilitate urine collection. Advantageously, the device 110 can be utilized to optimize urine collection in those patients that might otherwise need an indwelling Foley catheter.

Figure 20:
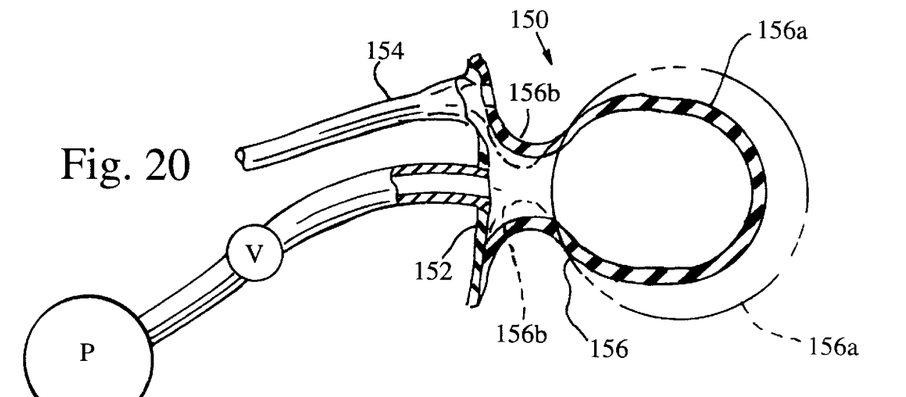
FIG. 20 is a side-view, partially in cross-section, of a urinary incontinence treatment device constructed in accordance with a fifth preferred embodiment of the present invention.
Figures 21, 22:
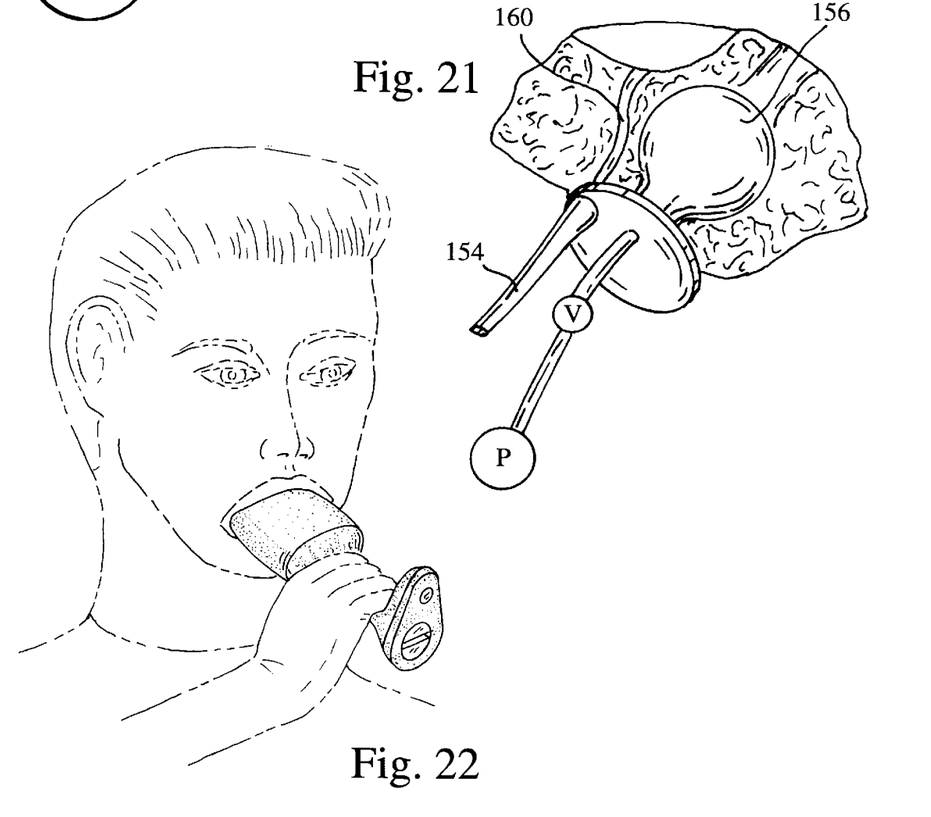
FIG. 21 is a perspective view of the device depicted in FIG. 20 as anchored within the vaginal lumen of the pelvic region.
FIG. 22 is a perspective view of the device constructed in accordance with a further embodiment of the present invention.

Referring now to FIGS. 20 and 21, there is shown an alternative embodiment of an incontinence treatment device 150 specifically designed and adapted to facilitate the drainage of urine from the bladder and urethra of a patient. As with embodiment depicted in FIGS. 15–19, the incontinence treatment device 150 comprises the combination of an annular panel member 152 having a port 154 formed thereon, the latter being designed to be aligned and sealed with the urethral meatus 160 of a patient, as shown in FIG. 21. Affixed to the annular seal member 152 is an anchor member 156, the latter being designed and configured to assume a first insertion configuration whereby such anchor member 156 can be positioned within the lumen of the anatomical passageway, and an anchor mode configuration, wherein such anchor 156 radially expands to compress and remain firmly seated within such passageway (as shown in phantom in FIG. 20.

In this regard, when in such an insertion mode, the anchor member has a reduced head or anchor portion 156a, which thus allows the same to become more easily inserted within an anatomical passageway. As shown in phantom, the anchor portion 156a can expand to thus compress against the lumen of such passageway, so as to cause the anchor to become firmly captured within the anatomical passageway.

As illustrated in FIG. 21, once inserted within the anatomical passageway, i.e., the vagina as shown, the anchor member 156 may be selectively expanded therewithin by use of such means as inflation via pressure P and valve V as shown, or any other means as well-known to those skilled in the art. Once anchored within the lumen of the anatomical passageway, the port 154 formed on annular seal member 152 may be aligned with the urethral meatus 160 such that the port 154 is sealed thereto to thus allow urine to pass therethrough.

In addition to serving as an anchoring means to facilitate urinary drainage, it should be understood by those skilled in the art that the anchor devices disclosed in each of the embodiments herein may further find widespread application as pessary devices to provide pelvic support as may be needed in a variety of medical conditions. In this regard, such anchor members, such as those depicted in FIG. 21, may be selectively inserted within an anatomical passageway and selectively expanded to a degree sufficient to provide the necessary support to such structures as the urethra.

Such anchor devices disclosed herein may further be selectively designed and adapted to not only optimize anatomical support and positioning, but may further be utilized to generate customized pessary devices to thus provide optimal structural support for a specific individual. In this regard, such anchor devices may be provided with apparatus, such as 200 depicted in FIG. 20, for determining the specific dimensions and contours of an anatomical passageway to which the same are inserted and designed to support. Specifically, such anchor devices or anatomical inserts may be utilized to determine the depth and width of a particular passageway to thus construct a three-dimensional model thereof. The data received from such apparatus can then be utilized to manufacture custom pessaries as that will provide optimal anatomical support to suit the specific needs of a given individual.

While the aforementioned detailed description is directed to pelvic anatomical passageways, and should be understood that various additions, deletions, modifications, and alterations may be made to the above-referenced described embodiments without the parting from the intended spirit and scope of the present invention. In this regard, it should be expressly understood that the indwelling device body described above with respect to the first three embodiments may be selectively modified for use against exit of the oral cavity, i.e., corners of the mouth, as illustrated as in FIG. 22, to facilitate the performance of known exercise regimens for facial muscles. In this regard, the various embodiments of the device of the present invention can be utilized to promote the performance of exercises that could improve the strength and tone of the various facial, chin and neck muscles which in turn could provide an improved facial appearance.

It is to be understood that the individual elements and components of each above-described embodiment may be interchanged among and/or incorporated into any and all embodiments of the invention, even though certain elements or components may have been mentioned or described herein with respect certain embodiment(s) of the invention only.

What is claimed is:

1. A device which is adapted to be inserted into a pelvic anatomical passageway of a human being to identify and target pelvic floor muscles and facilitate the performance of pelvic muscle strengthening exercises therefor, said device comprising:
   a) a device body sized and configured to be slidably inserted and anchored within said anatomical passageway, said device body being adapted to selectively exert a perceptible stimulus against a predetermined region of said anatomical passageway located adjacent to said device body; and
   b) a switching device formed with said device body for selectively and intermittently causing said device body to exert and cease exerting said perceptible stimulus.

2. The device of claim 1, wherein said device body is formed to have distal, intermediate, and proximal portions, said distal portion being sized and configured to be frictionally retained and anchored adjacent the inlet to said passageway and exert said perceptible stimulus thereto.

3. The device of claim 1 wherein:
   a) said distal portion of said device body is formed to have a generally arrowhead-shaped configuration;
   b) said intermediate portion of said device body is formed to have a generally shaft-shaped configuration; and
   c) said proximal portion of said device body is formed to have a handle portion formed thereon to facilitate manual manipulation of said device.

4. The device of claim 1 wherein said device further includes:
   d) a timer apparatus disposed within said device body and coupled to said switching device to enable such device to cause the device body to selectively exert said perceptible stimulus at predetermined times.

5. The device of claim 1 wherein said anatomical passageway is the vagina and wherein said device body is sized and configured for intra-vaginal insertion.

6. The device of claim 1 wherein said anatomical passageway is the anus and said device body is sized and configured for intra-anal insertion.

7. The device of claim 1 wherein said perceptible stimulus exerted by said device body is produced by a stimulus-producing device disposed within said device body.

8. The device of claim 7 wherein said stimulus producing device comprises a pressure-exerting device designed to be alternatively transitional between:

a) a rest mode configuration wherein said device causes the device body to exert no more than a baseline amount of pressure against a predetermined region of said anatomical passageway within which the device body is rotated adjacent to said device body; and b) an exercise mode configuration wherein said device causes the device body to exert more than the baseline amount of pressure against the predetermined region of the anatomical passageway, said pressure exerted in said exercise mode configuration being of sufficient degree to produce a perceptible stimulus.

9. The device of claim 7 wherein said stimulus producing device comprises a vibrator apparatus for causing at least a portion of said device body to vibrate.

10. A device which is adapted to be inserted into a pelvic anatomical passageway of a human being to identify pelvic floor muscles and facilitate the performance of pelvic muscle strengthening exercises, said device comprising:

a) a device body sized and configured to be slidably inserted and frictionally retained within said anatomical passageway, said device body being adapted to selectively exert a perceptible stimulus against a predetermined region of said anatomical passageway located adjacent to said device body; and b) a switching device coupled to said device body for selectively and intermittently causing said device body to exert and cease exerting said perceptible stimulus.

11. The device of claim 10 wherein said switching device is housed within a remote enclosure and coupled to said device body via an electrical cord to thus enable the switching device to be operated from outside the anatomical passageway within which the device body is retained.

12. The device of claim 10 wherein said device body is designed and adapted to exert first and second perceptible stimuli.

13. The device of claim 12 wherein said first perceptible stimulus is produced by a first stimulus producing device and said second perceptible stimulus is produced by a second stimulus producing device.

14. The device of claim 12 wherein said first stimulus producing device is selected from the group comprising a vibrator, and pressure-exerting device, wherein said pressure-exerting device is designed to be alternately transitional between:

a) a rest mode configuration wherein said device causes the device body to exert no more than a baseline amount of pressure against a predetermined region of said anatomical passageway within which the device body is rotated adjacent to said device body; and b) an exercise mode configuration wherein said device causes the device body to exert more than the baseline amount of pressure against the predetermined region of the anatomical passageway, said pressure exerted in said exercise mode configuration being of sufficient degree to produce a perceptible stimulus.

15. The device of claim 13 wherein said switching device is provided with dedicated switching members to selectively cause said first and second stimulus producing devices to exert a respective perceptible stimuli produced thereby.

16. The device of claim 14 wherein said switching device is provided with a timer coupled to said dedicated switching members for causing said members to selectively actuate said first and second stimulus producing devices at predetermined times.

17. A device adapted to be inserted into a pelvic anatomical passageway of a patient for facilitating the drainage of urine therefrom, said device comprising:

a) a base panel having a port formed thereon;

b) an anchor member affixed to said base panel for securing said device within said anatomical passageway, said anchor being so securable within the said passageway such that said panel member and port formed thereon are anatomically alignable with and sealable to the urethral meatus of the patient such that when such port is so aligned with such urethral meatus, a continuous conduit is defined through which urine may flow from the bladder and through said port.

18. The device of claim 17 wherein said anchor member comprises a generally mushroom-shaped cap member that is selectively deformable to assume a first insertion configuration whereby such anchor member is received within said anatomical passageway, and a second anchoring configuration whereby said anchor is caused to radially compress about said passageway to thus cause said device to remain seated therewithin.

19. The device of claim of 18 wherein said mushroom-shaped anchor member is caused to radially compress about said passageway when in said second anchoring configuration by radially inverting within said passageway.

20. The device of claim 17 wherein said base panel is rotatably connected to said anchor member such that said panel may be rotated to align said port formed thereon with said urethral meatus.

21. The device of claim 17 wherein said anchor member is designed and configured to be received and secured within the vagina.

22. The device of claim 17 wherein said anchor member is designed and configured to be received and secured within the anus.

23. The device of claim 17 wherein said anchor member comprises a head portion and a neck portion, said anchor member being selectively transitionable between an insertion configuration wherein said head portion assumes a first dimension and a second anchor configuration wherein said head portion assumes a size substantially greater than said first configuration.

24. The device of claim 22 wherein said anchor member is specifically designed and configured to provide structural support to said anatomical passageway when said anchor assumes said anchor configuration.

25. A device which is adapted to be inserted into the opening of the mouth of a human being to identify and target facial muscles and facilitate the performance of facial muscle strengthening exercises therefor, said device comprising:

a) a device body sized and configured to be slidably inserted and anchored within said opening of said patient's mouth, said device body being adapted to selectively exert a perceptible stimulus against a predetermined region of said opening of said patient's mouth located adjacent to said device body; and b) a switching device formed within said device body for selectively causing said device body to exert said perceptible stimulus.

26. A device which is adapted to be inserted into a pelvic anatomical passageway of a human being to identify and target pelvic floor muscles and monitor the performance of pelvic muscle strengthening exercises therefor, said device comprising:

a) a device body sized and configured to be slidably inserted and anchored within said anatomical passageway;

b) an exercise monitoring device disposed within said device body for monitoring the frequency and duration said target pelvic floor muscles are exercised and measure the progress made in the strengthening thereof.

27. The device of claim 26 wherein said exercise monitoring device is further designed to produce a biofeedback signal to facilitate a volitional performance of said pelvic muscle strengthening exercises.

28. A device for determining the contours and dimensions of an anatomical passageway comprising:

a) an insert member sized and configured to be slidably inserted within said anatomical passageway, said insert member being selectively expanded such that said insert member substantially conforms to the specific dimensions of said anatomical passageway within which said insert member is received; and b) a measuring apparatus coupled to said insert member for measuring the size and shape of said insert member when said insert member selectively assumes said size and dimensions of said anatomical passageway.

29. The device of claim 28 wherein said insert member selectively transitions between an insertion configuration wherein said insert member assumes a first size and shape, and a second measuring configuration wherein said insert member assumes said size and shape of said anatomical passageway within which said insert member is received.

30. The device of claim 28 wherein said measuring apparatus further designed to generate measurement and dimension data of said anatomical passageway wherein said measurement and dimension data is utilized to form a custom pessary device for placement within said anatomical passageway.

* * * * *